US012350200B2

United States Patent
Orrington, II et al.

(10) Patent No.: US 12,350,200 B2
(45) Date of Patent: Jul. 8, 2025

(54) PROTECTIVE APPARATUSES FOR MINIMIZING RISK OF TRANSMISSION OF INFECTION AND ASSOCIATED SYSTEMS

(71) Applicant: James L. Orrington, II D.D.S., P.C., Chicago, IL (US)

(72) Inventors: James L Orrington, II, Flossmoor, IL (US); Michael Prince, Chicago, IL (US); Hyunchul Kim, Chicago, IL (US)

( * ) Notice: Subject to any disclaimer, the term of this patent is extended or adjusted under 35 U.S.C. 154(b) by 1118 days.

(21) Appl. No.: 17/088,846

(22) Filed: Nov. 4, 2020

(65) Prior Publication Data
US 2021/0353469 A1     Nov. 18, 2021

Related U.S. Application Data

(63) Continuation-in-part of application No. 16/943,133, filed on Jul. 30, 2020, and a continuation-in-part of
(Continued)

(51) Int. Cl.
*A61F 9/04* (2006.01)
*A41D 13/11* (2006.01)
(Continued)

(52) U.S. Cl.
CPC .......... *A61F 9/045* (2013.01); *A41D 13/1184* (2013.01); *A61B 90/05* (2016.02);
(Continued)

(58) Field of Classification Search
CPC ...... A41D 13/1184; A61B 2017/00907; A61B 2090/309; A61B 2090/372;
(Continued)

(56) References Cited

U.S. PATENT DOCUMENTS

| 2,485,325 A | 10/1949 | Sloane |
| 2,726,054 A | 12/1955 | Lesley et al. |

(Continued)

FOREIGN PATENT DOCUMENTS

| CA | 2140718 A | 7/1996 |
| CN | 204788058 U | 11/2015 |

(Continued)

OTHER PUBLICATIONS

International Search Report for PCT Application No. PCT/US21/26324, dated Jul. 22, 2021; and associated written opinion.
(Continued)

*Primary Examiner* — Charles A Marmor, II
*Assistant Examiner* — Marc D. Honrath
(74) *Attorney, Agent, or Firm* — Chiacchio IP, LLC; Theodore J. Chiacchio

(57) ABSTRACT

A protective apparatus is provided for minimizing the risk of transmission of SARS-CoV-2 and/or other infectious diseases between individuals in close proximity to one another, such as by transmission through droplets projecting from the mouth or nasal region of an infected individual. The protective apparatus may include a shield component that can be transparent, a handle component with a connecting aspect, light emitting diodes, and a control console for controlling functions of the protective apparatus. The protective apparatus may include a camera communicatively connected to a display screen that can display images captured by the camera.

7 Claims, 10 Drawing Sheets

Related U.S. Application Data application No. 16/943,178, filed on Jul. 30, 2020, said application No. 16/943,133 is a continuation of application No. 16/924,649, filed on Jul. 9, 2020, said application No. 16/943,178 is a continuation of application No. 16/924,649, filed on Jul. 9, 2020.

(60) Provisional application No. 63/026,110, filed on May 17, 2020.

(51) Int. Cl.
*A61B 90/00* (2016.01)
*A61B 90/30* (2016.01)
*A61C 19/00* (2006.01)
*A61G 15/10* (2006.01)

(52) U.S. Cl.
CPC ............ *A61B 90/30* (2016.02); *A61B 90/361* (2016.02); *A61C 19/00* (2013.01); *A61G 15/10* (2013.01); *A61B 2090/372* (2016.02); *A61H 2201/1604* (2013.01)

(58) Field of Classification Search
CPC ... A61B 2090/401; A61B 50/00; A61B 90/05; A61B 90/30; A61B 90/36; A61B 90/361; A61B 90/40; A61C 19/00; A61F 9/045; A61G 15/10; A61G 15/14; A61H 2201/1604

See application file for complete search history.

(56) References Cited

U.S. PATENT DOCUMENTS

| | | |
|---|---|---|
| 3,377,082 A | 4/1968 | Saunders |
| 3,877,691 A | 4/1975 | Foster |
| 4,444,183 A | 4/1984 | Heckendorn |
| 4,559,939 A | 12/1985 | Levine et al. |
| 4,734,625 A * | 3/1988 | Geanous ............... H05B 47/29 315/312 |
| 4,777,574 A * | 10/1988 | Eisner ................... A61B 46/10 362/399 |
| 4,781,108 A | 11/1988 | Nillson |
| 4,832,042 A | 5/1989 | Poppendiek et al. |
| 4,936,318 A | 6/1990 | Schoolman |
| 4,942,685 A * | 7/1990 | Lin ...................... A47G 1/0622 40/716 |
| 4,949,714 A | 8/1990 | Orr |
| 5,012,852 A | 5/1991 | Blackhurst |
| 5,316,541 A | 5/1994 | Fischer |
| D354,560 S | 1/1995 | Chase |
| 5,497,295 A * | 3/1996 | Gehly ................. G02B 6/4298 362/427 |
| 5,620,407 A | 4/1997 | Chang |
| 5,636,627 A | 6/1997 | Rochester |
| 5,865,182 A | 2/1999 | Chen |
| 6,309,222 B1 | 10/2001 | Billingsley |
| 6,321,764 B1 | 11/2001 | Gauger et al. |
| 6,322,754 B1 | 11/2001 | Buchmann et al. |
| 6,338,675 B2 | 1/2002 | Winkelman |
| 6,367,943 B1 | 4/2002 | Tocci et al. |
| 6,471,579 B1 | 10/2002 | Blackshear |
| 6,899,668 B2 | 5/2005 | Paranjpe |
| 7,094,266 B2 | 8/2006 | Montgomery |
| 7,503,890 B2 | 3/2009 | Kubicsko et al. |
| 8,087,341 B2 | 1/2012 | Adler |
| 8,234,822 B2 | 8/2012 | Proctor et al. |
| 8,245,713 B2 | 8/2012 | Paschal, Jr. et al. |
| 8,397,725 B2 | 3/2013 | Slaker et al. |
| 8,568,501 B2 | 10/2013 | Kelso |
| D704,934 S | 5/2014 | Blinka et al. |
| D784,541 S | 4/2017 | Hilbig et al. |
| 9,981,351 B2 | 5/2018 | Vanier |
| 10,016,251 B2 | 7/2018 | Holman et al. |
| 10,016,252 B1 | 7/2018 | Wren |
| 10,420,386 B1 | 9/2019 | Jefferis et al. |
| 10,596,282 B2 | 3/2020 | Gil et al. |
| 10,888,479 B1 | 1/2021 | Gershon et al. |
| 10,925,561 B2 | 2/2021 | Snow |
| D912,842 S | 3/2021 | Chou et al. |
| D920,518 S | 5/2021 | Takahashi |
| D926,462 S | 8/2021 | Burgon et al. |
| D936,905 S | 11/2021 | Jefferis et al. |
| 11,191,334 B2 | 12/2021 | Aghazadeh et al. |
| D940,565 S | 1/2022 | Nguyen et al. |
| D947,679 S | 4/2022 | Hughes et al. |
| 11,317,986 B1 | 5/2022 | Ahearn |
| 11,534,256 B2 | 12/2022 | Asamaral |
| 2004/0129860 A1 * | 7/2004 | Thibaud .............. F21V 23/0457 250/205 |
| 2004/0177447 A1 | 9/2004 | Love |
| 2004/0255937 A1 | 12/2004 | Sun |
| 2005/0011035 A1 | 1/2005 | Rukavina et al. |
| 2005/0085686 A1 | 4/2005 | Yuen et al. |
| 2005/0285547 A1 * | 12/2005 | Piepgras ................ H05B 45/20 315/294 |
| 2006/0148397 A1 | 7/2006 | Schultz et al. |
| 2006/0247487 A1 | 11/2006 | Arts et al. |
| 2007/0125224 A1 | 6/2007 | Thomas |
| 2008/0033328 A1 | 2/2008 | Chang |
| 2008/0212337 A1 | 9/2008 | Mangiardi |
| 2008/0223384 A1 | 9/2008 | Zabari |
| 2009/0088061 A1 | 4/2009 | Le Beau |
| 2010/0279594 A1 | 11/2010 | Peeler et al. |
| 2011/0202068 A1 * | 8/2011 | Diolaiti ................. A61B 34/30 606/130 |
| 2011/0226123 A1 | 9/2011 | Priebe et al. |
| 2011/0318702 A1 | 12/2011 | Lockwood |
| 2012/0326627 A1 * | 12/2012 | McDaniel, Jr. ........ H05B 45/20 315/294 |
| 2013/0101953 A1 | 4/2013 | Stone et al. |
| 2014/0111977 A1 | 4/2014 | Nyberg |
| 2014/0316455 A1 | 10/2014 | Gnanashanmugam |
| 2014/0349561 A1 | 11/2014 | Reiss et al. |
| 2015/0025300 A1 | 1/2015 | Hill et al. |
| 2016/0074268 A1 | 3/2016 | Breegi et al. |
| 2016/0249810 A1 | 9/2016 | Darty et al. |
| 2016/0341415 A1 * | 11/2016 | Lumaye ................... A47G 1/02 |
| 2016/0353055 A1 * | 12/2016 | Popescu ................. G16H 80/00 |
| 2017/0208878 A1 | 7/2017 | Kakinuma |
| 2018/0023799 A1 | 1/2018 | Lumaye et al. |
| 2018/0163978 A1 | 6/2018 | Ziegler et al. |
| 2018/0236614 A1 | 8/2018 | Holmes |
| 2019/0105740 A1 | 4/2019 | Vanier |
| 2019/0330874 A1 | 10/2019 | Pescovitz |
| 2019/0388290 A1 | 12/2019 | Comunale |
| 2020/0000541 A1 | 1/2020 | Clemens |
| 2020/0004676 A1 | 1/2020 | Kubota |
| 2020/0016774 A1 | 1/2020 | Keen |
| 2021/0290793 A1 | 9/2021 | Tung |
| 2021/0330419 A1 | 10/2021 | Danner |
| 2021/0346564 A1 | 11/2021 | Jetter |
| 2021/0353380 A1 | 11/2021 | Sellars et al. |
| 2021/0353469 A1 | 11/2021 | Orrington, II |
| 2022/0084199 A1 | 3/2022 | Lee et al. |
| 2022/0142269 A1 | 5/2022 | Orrington, II et al. |

FOREIGN PATENT DOCUMENTS

| | | |
|---|---|---|
| CN | 106581867 | 4/2017 |
| CN | 210472180 | 5/2020 |
| EP | 0463282 A1 | 1/1992 |
| EP | 3895653 | 10/2021 |
| EP | 4093317 A4 | 2/2024 |
| EP | 4142643 A4 | 7/2024 |
| IN | 427 | 4/2010 |
| JP | H0549688 A | 3/1993 |
| JP | H06038933 | 5/1994 |
| JP | H08033659 | 2/1996 |
| JP | 2002303436 A | 10/2002 |
| JP | 2007130333 | 5/2007 |
| JP | 2015037475 A | 2/2015 |
| JP | 2016086839 A | 5/2016 |

(56) References Cited

FOREIGN PATENT DOCUMENTS

| JP | 1683418 S | 4/2021 |
|---|---|---|
| KR | 20150033913 | 4/2014 |
| RU | 80336 U1 | 2/2009 |
| RU | 2008138178 U | 2/2009 |
| WO | WO 2021236241 A1 | 11/2021 |
| WO | WO 2021236245 A1 | 11/2021 |

OTHER PUBLICATIONS

Dentistry biggest problem has been solved! AirguardTM, Airguard, Youtube, [Post date: Feb. 24, 2021], [Site seen May 26, 2022], Seen at URL: https://www.youtube.com/watch?v=ARYY-09G.

Dental Face Shield, Classical Designs, [Post Date unknown], [Site seen May 26, 2022], Seen at URL: https://glassicaldesigns.com/product/dental-face-shield/ (Year: 2022).

By Anahad O'connor; Really? Flu Is Spread Primarily Through Close Contact; published Feb. 11, 2013; The New York Times (Year: 2013).

Airguard LT. Airguard, [Post date: Feb. 15, 2021], [Site seen May 26, 2022], Seen at URL: https://mobile.twitter.com/AirGuardHealth/status/1361314680480927750?cxt=HHwWjMC42aif.

* cited by examiner

PROTECTIVE APPARATUSES FOR MINIMIZING RISK OF TRANSMISSION OF INFECTION AND ASSOCIATED SYSTEMS

CROSS-REFERENCE TO RELATED APPLICATIONS

The present application is a continuation-in-part of, and claims the benefit of and priority to, U.S. patent application Ser. Nos. 16/943,133 and 16/943,178, both filed on Jul. 30, 2020 and both of which claim the benefit of and priority to U.S. patent application Ser. No. 16/924,649, filed on Jul. 9, 2020. Each of the above-identified patent applications, including the present application, also claims the benefit of and priority to U.S. Provisional Patent Application No. 63/026,110, filed on May 17, 2020. The contents of each of the above-referenced applications are incorporated herein by reference.

FIELD OF THE INVENTION

The present disclosure relates to protective apparatuses and associated systems designed to minimize the risk of transmission of the COVID-19 virus and/or other sources of infection in environments where there is a high risk of transmission due to individuals being in close physical proximity to one another. More particularly, the disclosure relates to protective apparatuses comprising a substantially transparent shield component and a handle component comprising a connecting aspect installable to, without limitation, a vacuum hose or other substantially cylindrical object.

BACKGROUND

COVID-19 is an infectious disease caused by severe acute respiratory syndrome coronavirus 2 (SARS-CoV-2). The first cases of COVID-19 were reported in December, 2019, in Wuhan, China. Since that time, the virus has spread throughout the world, resulting in a global pandemic. More than 41 million patients have been diagnosed with COVID-19 across more than 213 countries and territories. As of the date of this disclosure, there have been more than 1.1 million reported deaths due to COVID-19.

COVID-19 may be transmitted via droplet contact (e.g., coughing and sneezing); direct physical contact; indirect physical contact (e.g., touching a contaminated surface); and airborne transmission. The primary way through which COVID-19 is transmitted, however, is through small droplets produced by coughing, sneezing, and talking, where individuals are in close physical proximity to one another. COVID-19 may be transmitted by persons infected with the virus who have not exhibited any symptoms. Future effects of COVID-19 remain in question, as no known solution exists to mitigate or eliminate these undesirable conditions conducive to ongoing transmission.

Close physical proximity between people increases the risk of transmitting COVID-19 because COVID-19 may be transmitted via at least droplet contact (e.g., coughing and sneezing); direct physical contact; indirect physical contact (e.g., touching a contaminated surface); and airborne transmission. Social distancing, also referred to as physical distancing, is one of the primary tactics that have been utilized throughout the world to attempt to contain the spread of the COVID-19 virus. Social distancing comprises maintaining certain minimum physical distances between individuals and reducing the number of times that individuals come into close physical contact with one another. However, not all activities permit of maintaining sufficient minimum physical distances. For example, many healthcare workers must come within close proximity to their patients in order to perform their duties. Where close physical proximity between people cannot be avoided, there exists a need for a system that is effective in reducing the risk of transmitting COVID-19.

Particles are classified based on size. Coarse particles are 2.5 to 10 microns. Fine particles are less than 2.5 microns. Ultrafine particles are those less than 0.1 microns in size. A human nose generally filters particles larger than 10 microns. If a particle is less than 10 microns, it can enter the respiratory system. If a particle is less than 2.5 microns, it can enter the alveoli. An ultrafine particle can enter the bloodstream and target organs. COVID-19 exists as ultrafine particles.

Current research suggests that most respiratory transmission of COVID-19 occurs through large respiratory droplets. Such large droplets typically fall to the ground after travelling approximately six feet at the most. Activity such as coughing and sneezing, however, can aerosolize the droplets so that they can travel further thereby increasing the risk of transmission (i.e., where the droplets are carrying COVID-19). When aerosolized, COVID-19 can travel up to approximately 20 feet and will remain suspended in the air longer than when not aerosolized. In addition to coughing and sneezing, respiratory droplets are routinely aerosolized in the practice of dentistry.

Dentists who utilize aerosolization in their practice, and therefore their staff as well, are at a high risk of becoming infected with COVID-19. Such dentists' patients are likewise at high risk of becoming infected from the dentist, as well as their dental assistants in the immediate area when being treated. Most such risk results from splatter and droplet transmission to the mid-face of the dentist and assistant and to the nasal area of the patient. Those of skill in the art will appreciate that individuals in other professions may realize the advantages of protective apparatuses and associated systems enabled by this disclosure such as, without limitation, other healthcare professionals who may, in the course of their work, come into close proximity with the nasal and mouth region of individuals whom they are treating.

SUMMARY

Protective apparatuses enabled by this disclosure advantageously solve deficiencies known in the current state of the art. According to an embodiment enabled by this disclosure, a protective apparatus is provided that advantageously enhances effectiveness in reducing the risk of transmitting COVID-19 or other infectious disease by mitigating direct, indirect, and/or other contact between individuals. Non-limiting examples of such indirect contact include, without limitation, projection of droplets and other fluids from a patient's mouth or nose onto or near a healthcare worker treating the patient. Another non-limiting example of such indirect contact includes where two individuals are in sufficiently close physical proximity to one another that one individual inhales air exhaled by the other individual. According to an embodiment enabled by this disclosure, a protective apparatus is provided that comprises a substantially transparent shield component and a handle component, wherein the handle component further comprises a connecting aspect. The connecting aspect may be secured to a suctioning device including, without limitation, a substantially cylindrical vacuum hose. According to an embodiment enabled by this disclosure, a protective apparatus is provided that comprises a camera communicatively connected to a display screen. In another aspect, the protective apparatus may further comprise light emitting diodes. These light emitting diodes may be located along one or more sides of the protective apparatus and/or may be located at the corners or other junctures where sides of the protective apparatus adjoin. According to an embodiment enabled by this disclosure, protective apparatuses as described herein may be connected to an articulating mechanical arm. The articulating arm may be positioned so as to locate the protective apparatus overtop an individual such as a dental patient to facilitate optimal treatment conditions wherein a dentist or other healthcare worker may treat the patient under conditions that minimize the risk of transmission of COVID-19 or other infectious disease.

DETAILED DESCRIPTION

Figure 1:
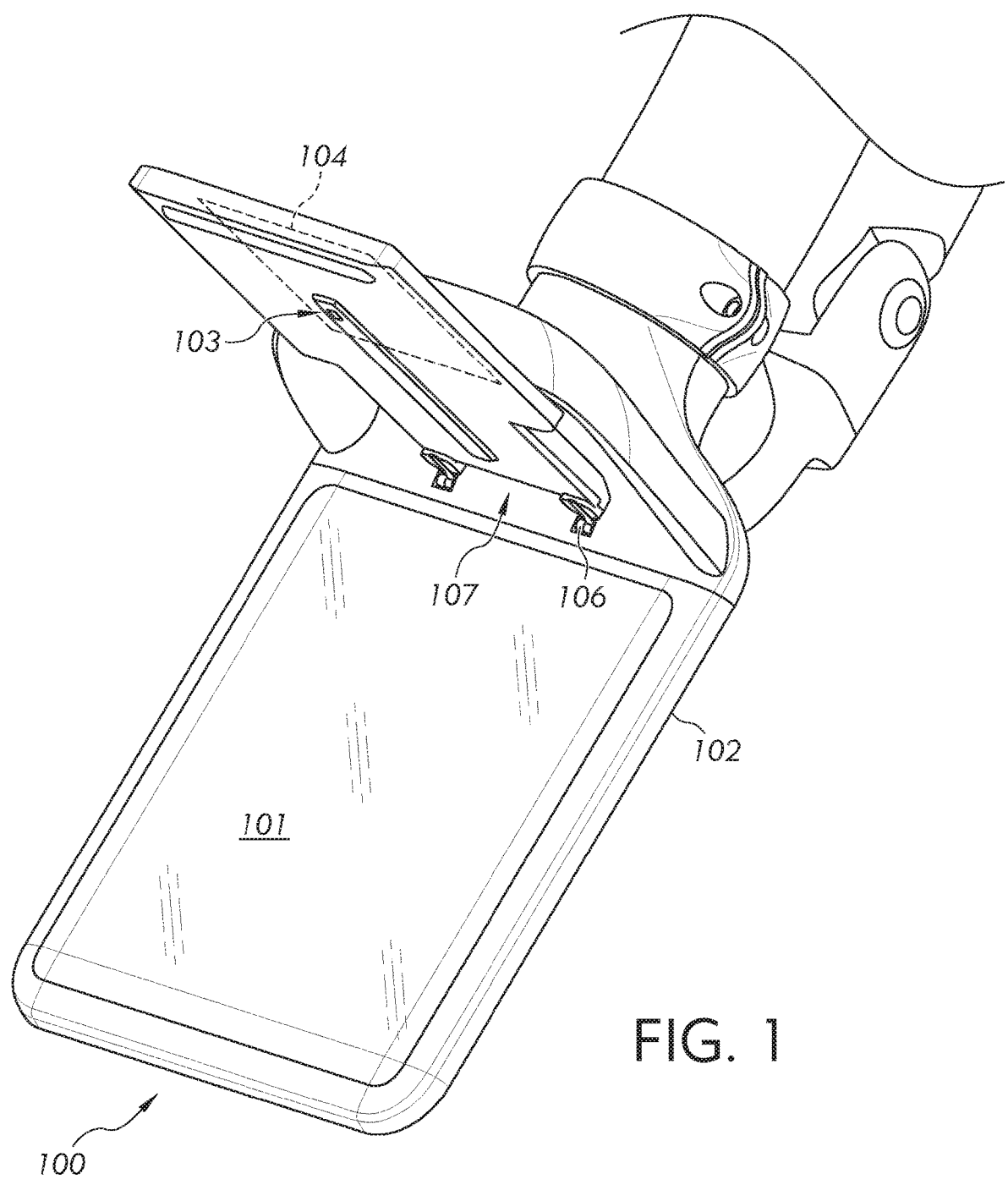
FIG. 1 is a top perspective view of a protective apparatus of the present disclosure.
Figure 2:
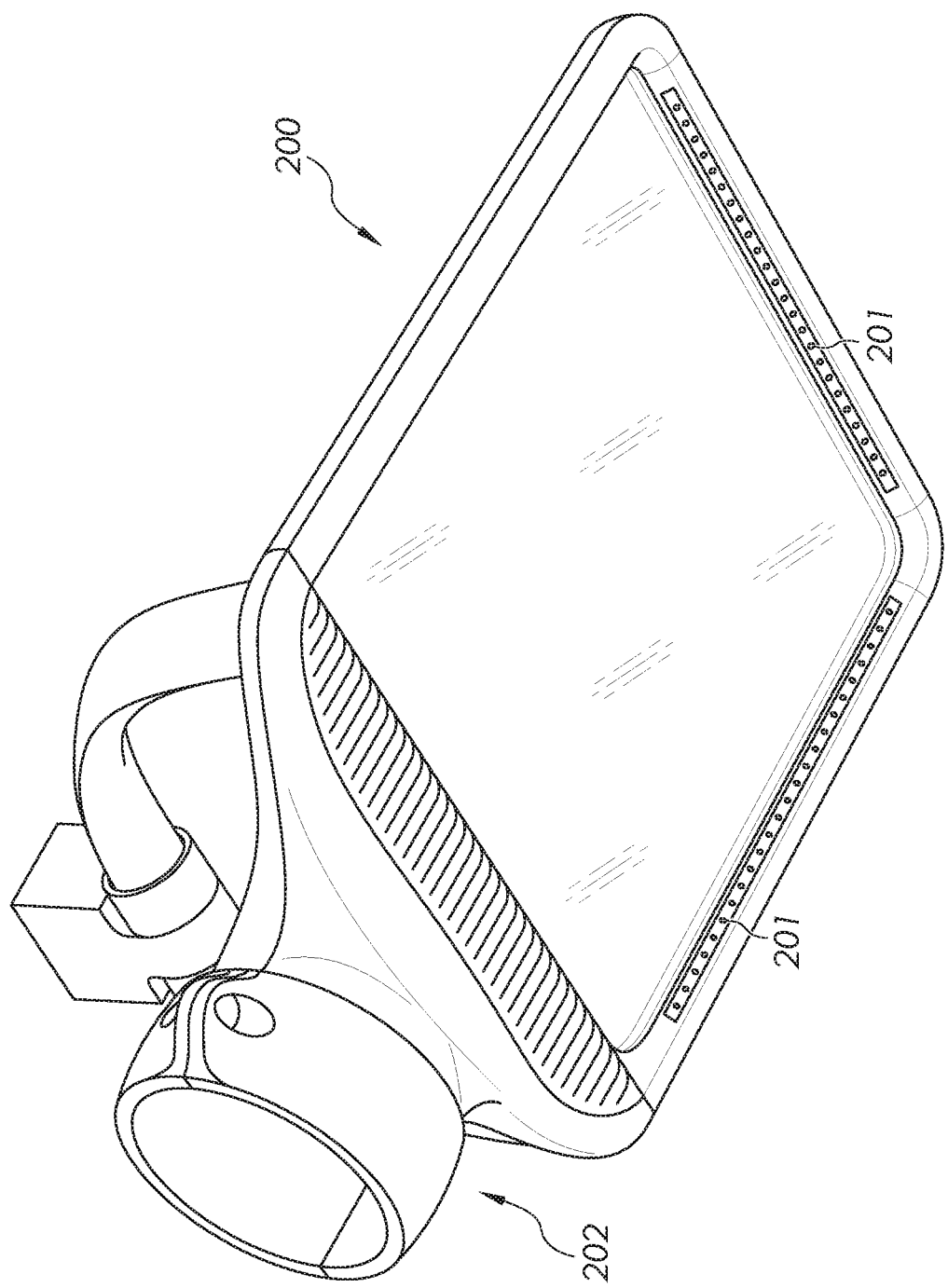
FIG. 2 is a bottom perspective view of a protective apparatus of the present disclosure.
Figure 3:
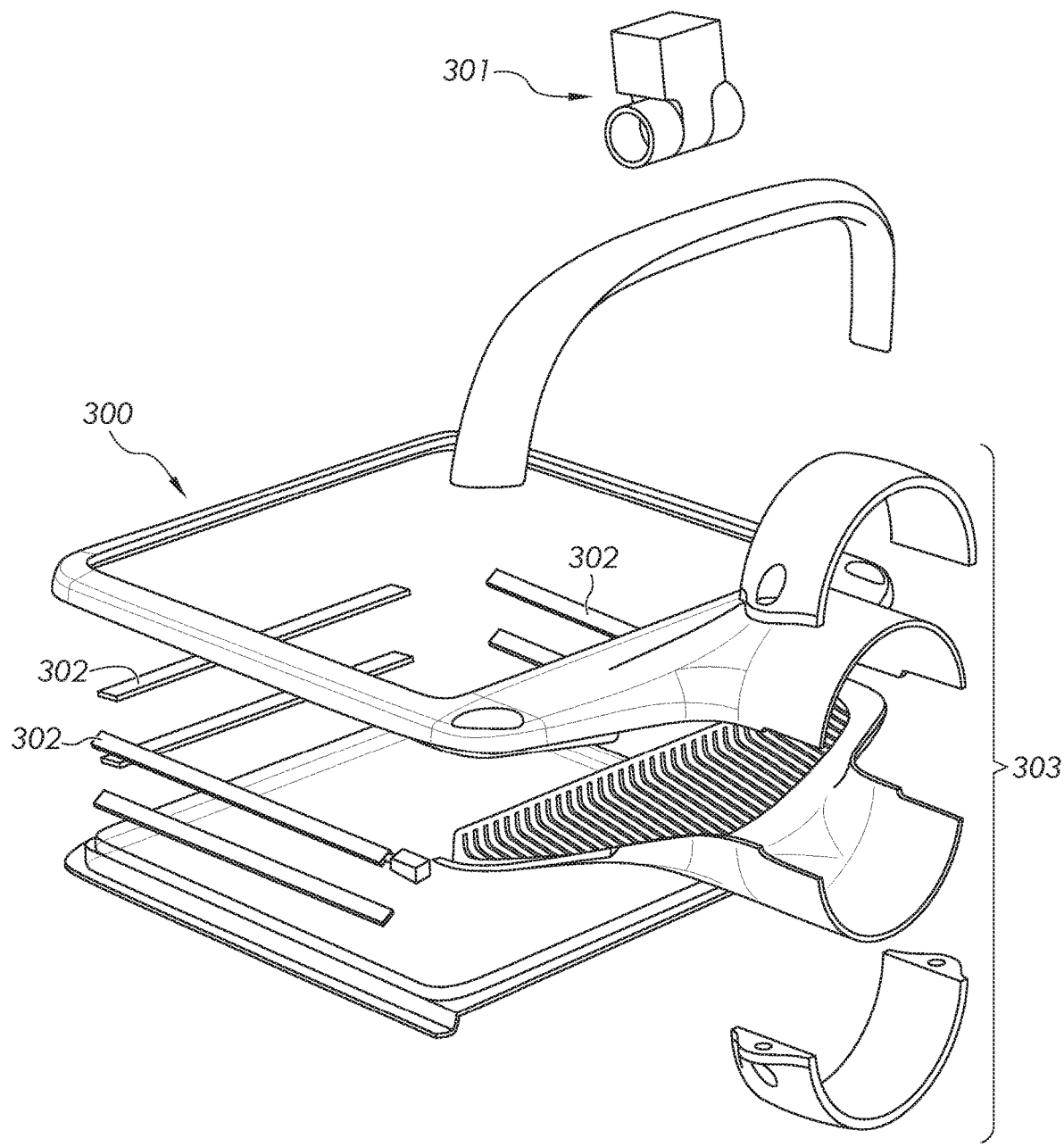
FIG. 3 is an exploded view of a protective apparatus of the present disclosure.
Figure 4:
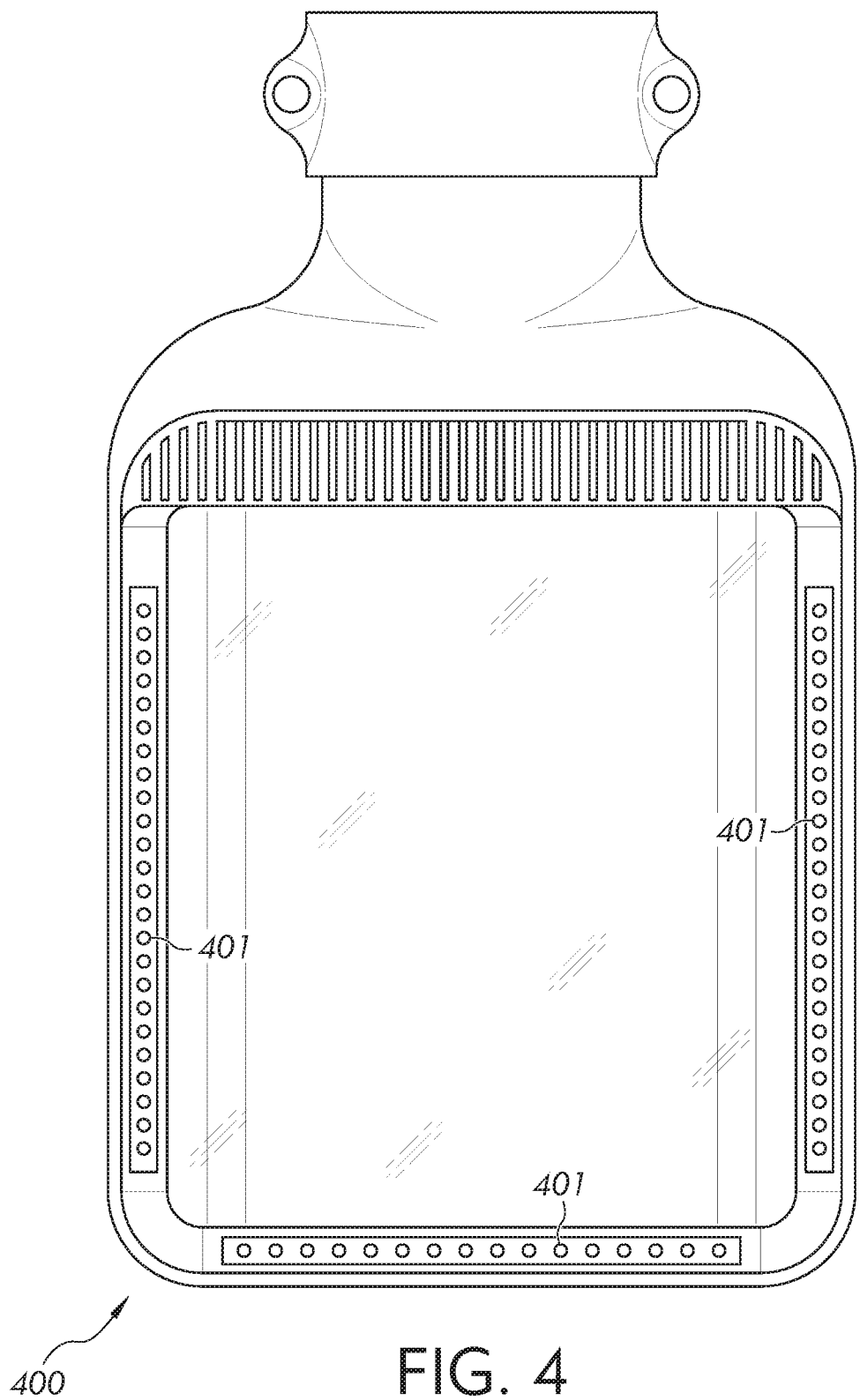
FIG. 4 is a bottom plan of a protective apparatus of the present disclosure.
Figure 5:
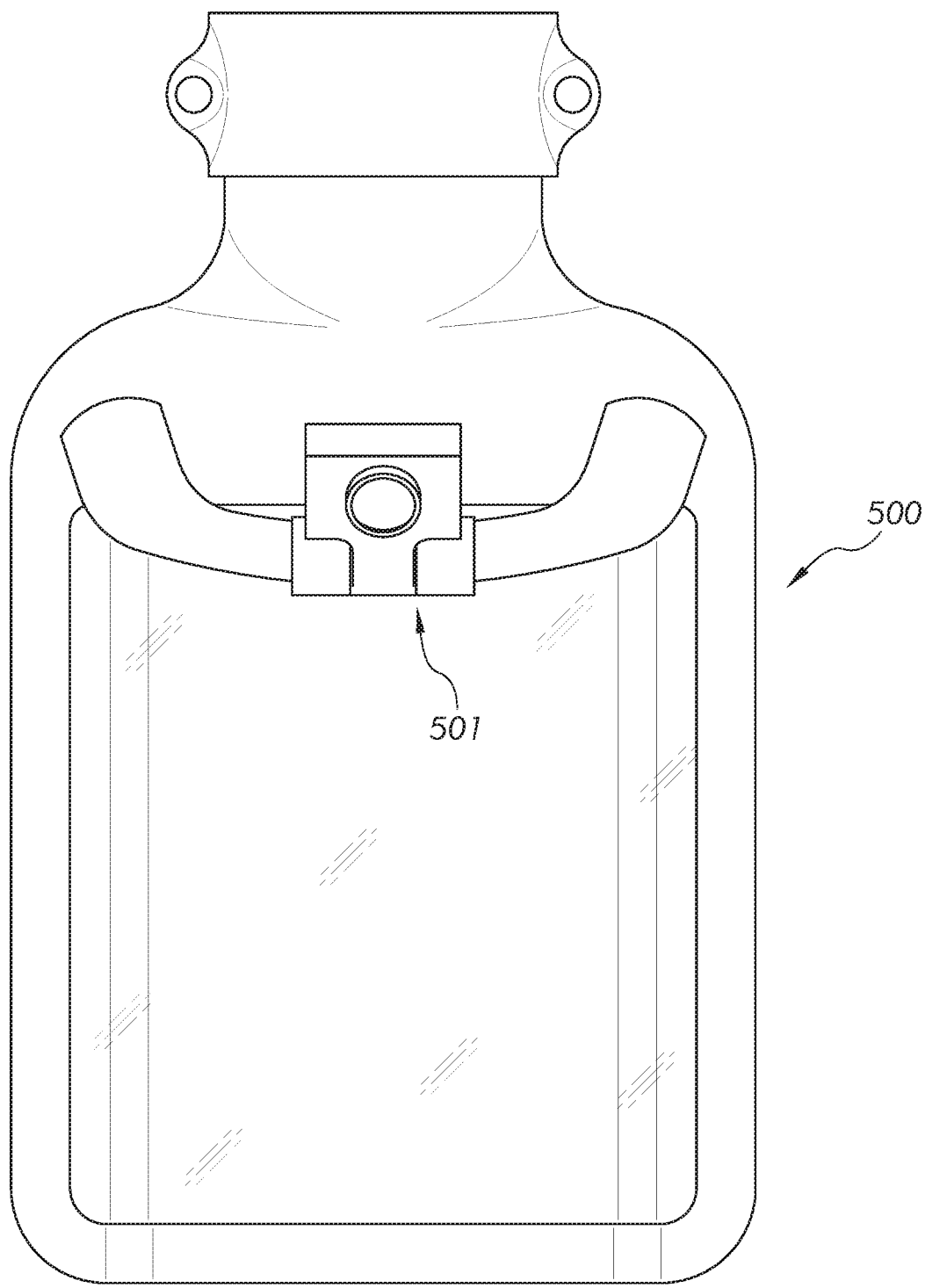
FIG. 5 is a top plan view of a protective apparatus of the present disclosure.
Figure 6:
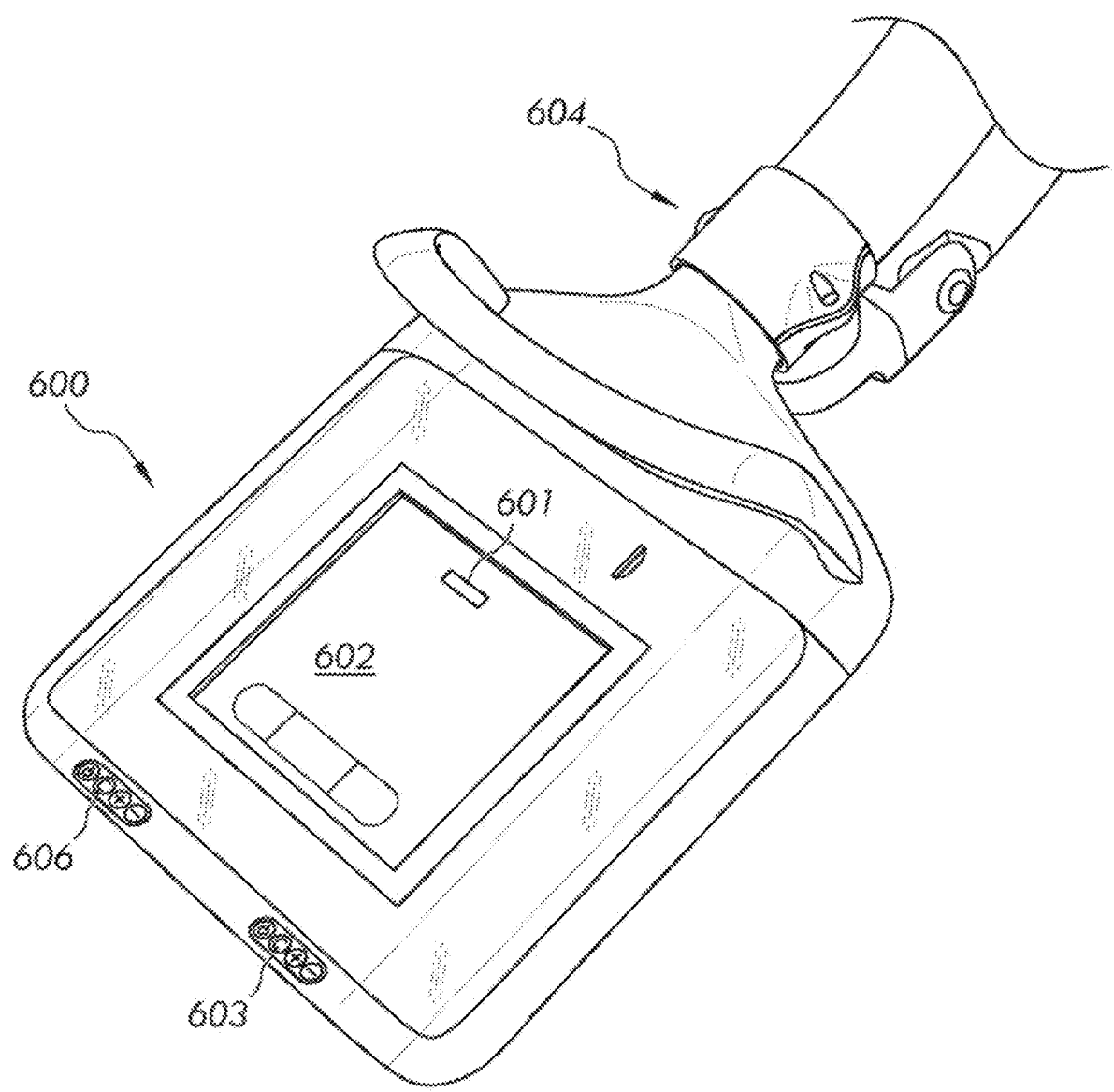
FIG. 6 is a top perspective view of a protective apparatus of the present disclosure.
Figure 7:
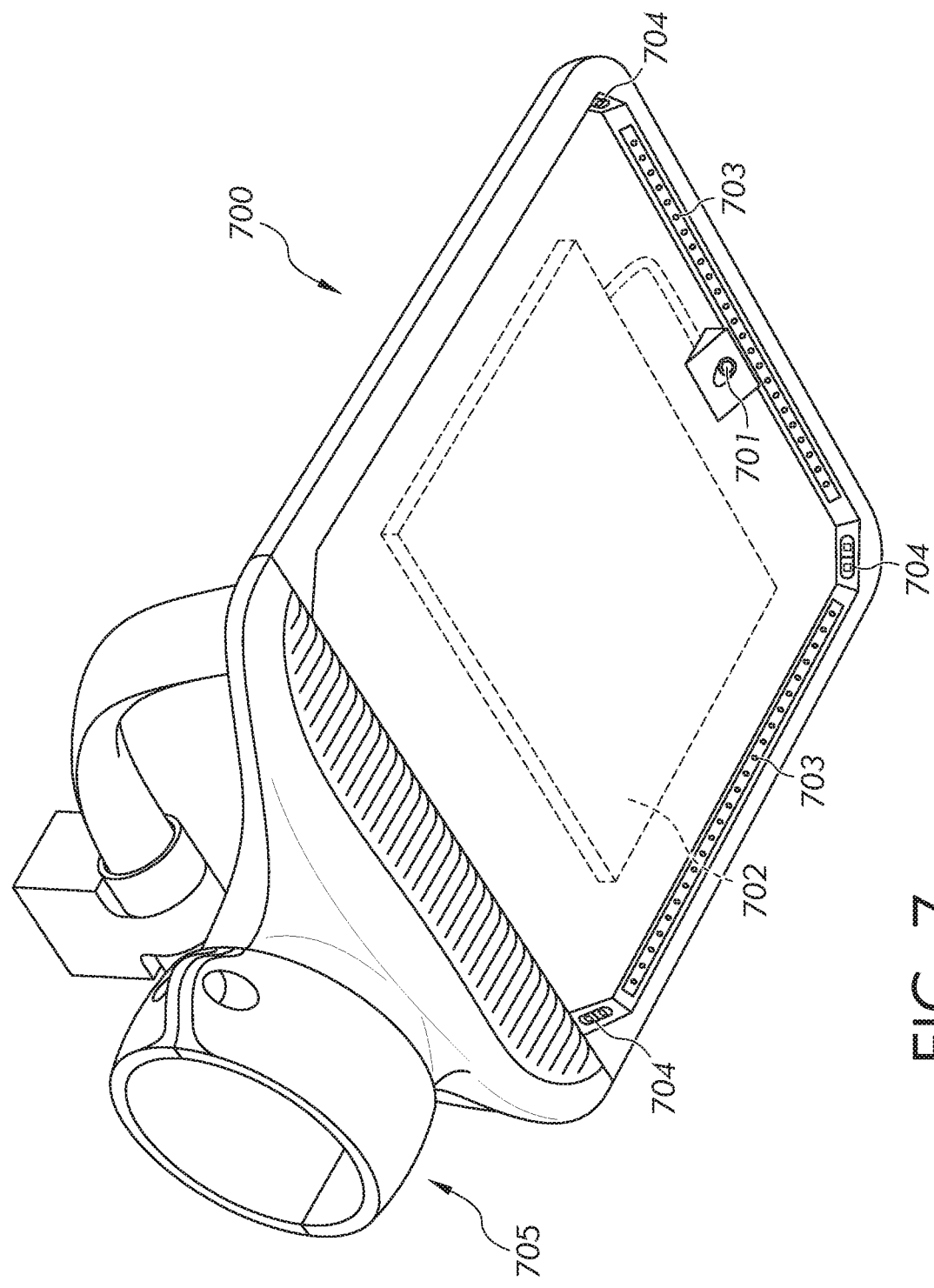
FIG. 7 is a bottom perspective view of a protective apparatus of the present disclosure.
Figure 8:
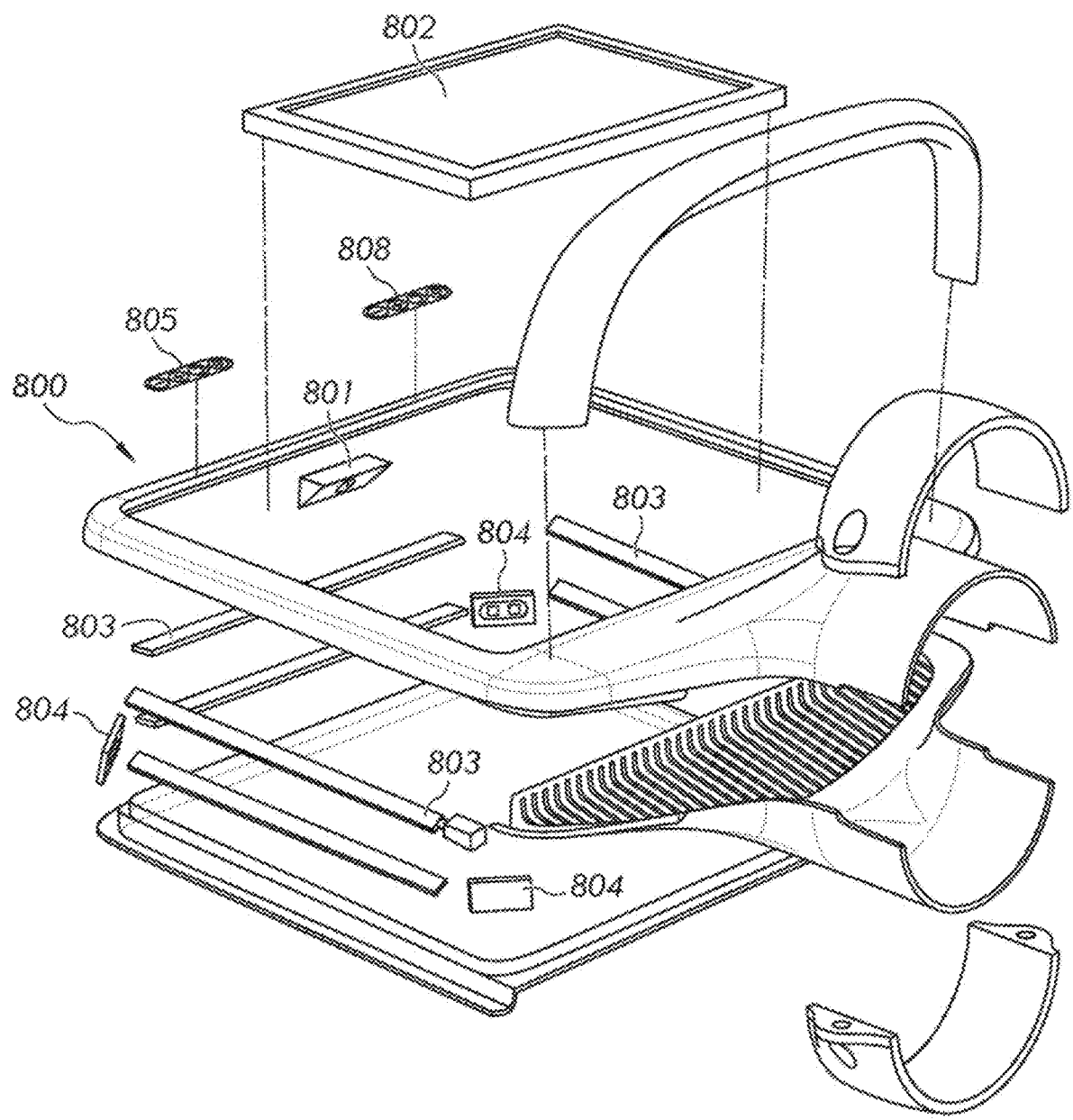
FIG. 8 is an exploded view of a protective apparatus of the present disclosure.
Figure 9:
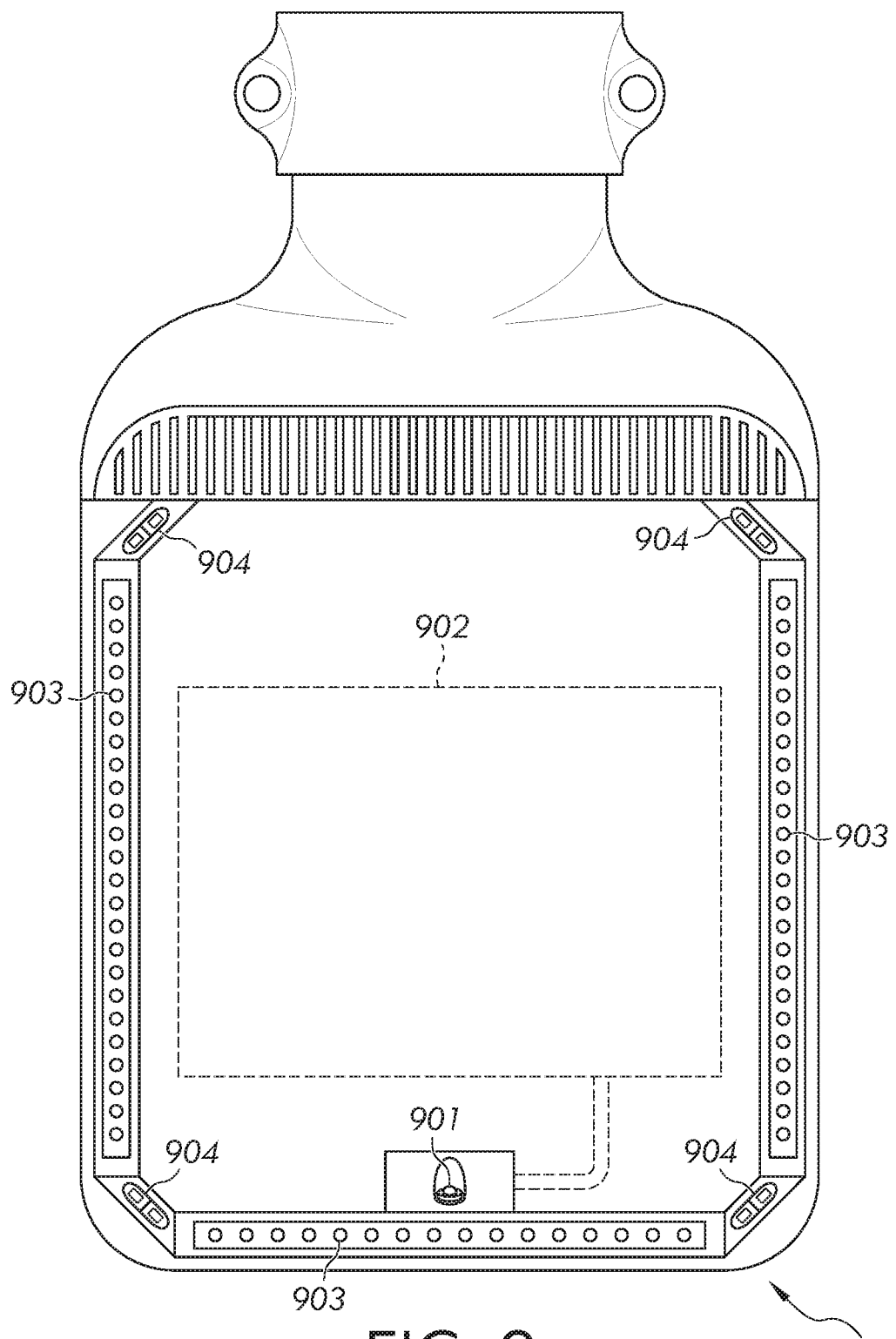
FIG. 9 is a bottom plan view of a protective apparatus of the present disclosure.
Figure 10:
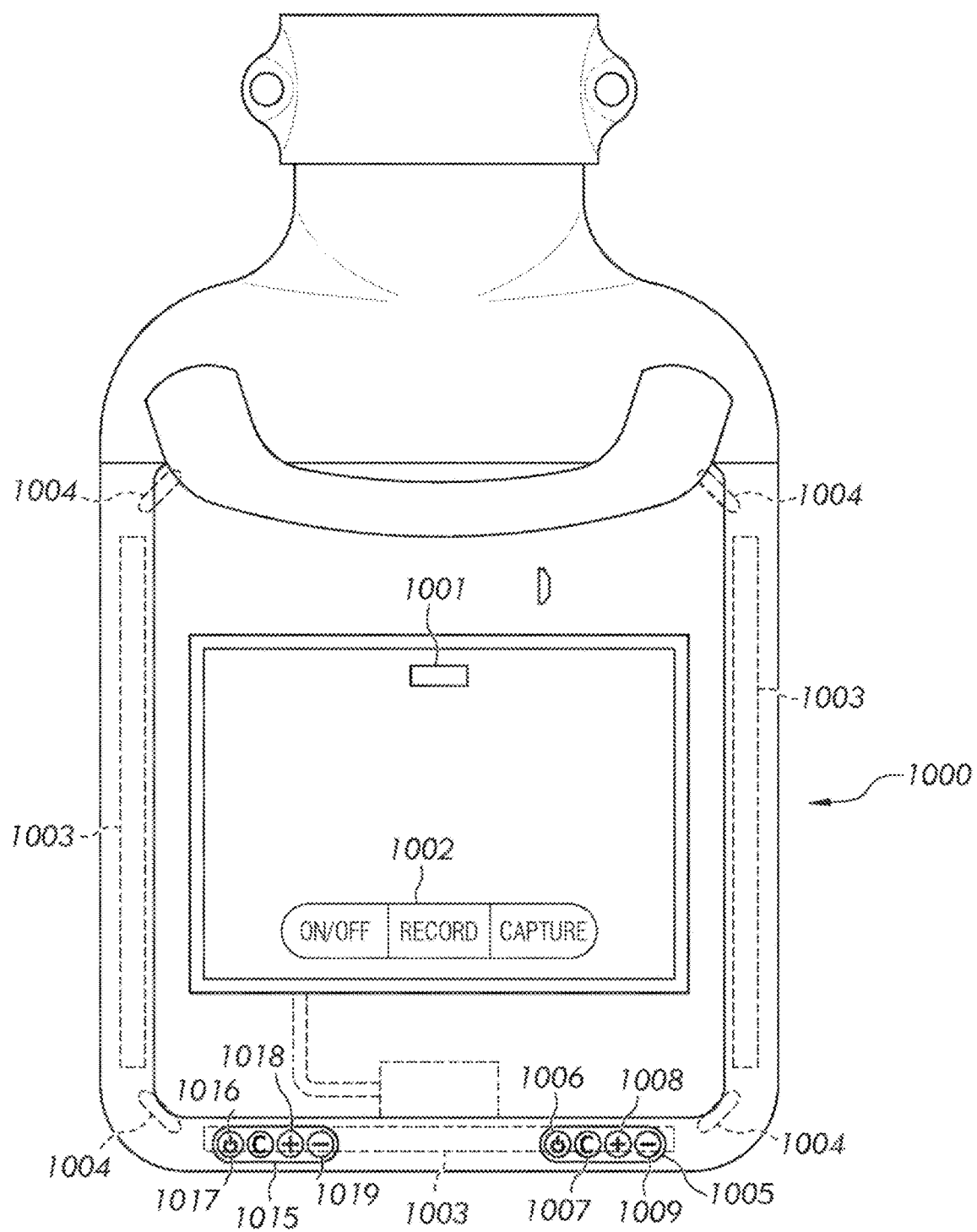
FIG. 10 is a top plan view of a protective apparatus of the present disclosure.

The following disclosure is provided to describe various embodiments of a protective apparatus intended to minimize the risk of transmission of COVID-19 and other viruses and infectious agents that may be transmitted between individuals in close physical proximity and/or who may interact with common surfaces or objects. Skilled artisans will appreciate additional embodiments and uses of the apparatuses that extend beyond the examples of this disclosure. Terms included by any claim are to be interpreted as defined within this disclosure. Singular forms should be read to contemplate and disclose plural alternatives. Similarly, plural forms should be read to contemplate and disclose singular alternatives. Conjunctions should be read as inclusive except where stated otherwise.

Expressions such as "at least one of A, B, and C" should be read to permit any of A, B, or C singularly or in combination with the remaining elements. Additionally, such groups may include multiple instances of one or more elements in that group, which may be included with other elements of the group. All numbers, measurements, and values are given as approximations unless expressly stated otherwise.

Terms and expressions used throughout this disclosure are to be interpreted broadly. Terms are intended to be understood respective to the definitions provided by this specification. Technical dictionaries and common meanings understood within the applicable art are intended to supplement these definitions. In instances where no suitable definition can be determined from the specification or technical dictionaries, such terms should be understood according to their plain and common meaning. However, any definitions provided by the specification will govern above all other sources.

Various objects, features, aspects, and advantages described by this disclosure will become more apparent from the following detailed description, along with the accompanying drawings.

For the purpose of clearly describing the components and features discussed throughout this disclosure, some frequently used terms will now be defined, without limitation. The term "COVID-19," as it is used throughout this disclosure, is defined as an infectious disease caused by severe acute respiratory syndrome coronavirus 2 (SARS-CoV-2). The term "aerosol," as it is used throughout this disclosure, is defined as a suspension of fine solid particles or liquid droplets in air or another gas. The term "universal mount," as it is used throughout this disclosure, is defined as a universal clamp together with one or more compatible mounts. The term "individual," as it is used throughout this disclosure, should not be interpreted in any limiting manner, should be interpreted broadly, and should be interpreted, without limitation, as synonymous with "subject." The term "LED(s)," as it is used throughout this disclosure, is defined as light emitting diodes.

Various aspects of the disclosure will now be described in detail, without limitation. In the following disclosure, protective apparatuses for minimizing risk, such as due to individuals' close physical proximity to one another, of transmission of COVID-19 and/or other infectious diseases will be discussed. Those of skill in the art will appreciate that alternative labeling of the apparatuses may be provided, which is consistent with the scope and spirit of this disclosure. Skilled readers should not view the inclusion of any alternative labels as limiting in any way.

Protective apparatuses contemplated by the present disclosure 100, 200, 300, 400, 500, 600, 700, 800, 900, 1000 may be operatively attached to a number of objects including, without limitation, a substantially cylindrical object such as a vacuum hose or other, similarly shaped suction device. In another embodiment, protective apparatuses contemplated by the present disclosure may be operatively attached to an articulating mechanical arm. A protective apparatus enabled by this disclosure may be attached to said objects by any suitable connecting means, which means would be readily appreciated by those skilled in the art. Such means may include, without limitation, a universal mount.

The protective apparatus enabled by this disclosure may comprise a substantially transparent shield component 101 and a handle component 102.

The substantially transparent shield component of the present disclosure may be substantially flat or may be curved. The substantially transparent shield component of the present disclosure may comprise protrusions to accommodate the curvature of an individual's face such as where said shield component is placed over an individual occupying a chair, such as a dental patient occupying a dentist's chair.

The substantially transparent shield component of the present disclosure may be removable from the protective apparatuses enabled by this disclosure so as to facilitate the washing of said shield component and the replacement of said shield component.

The substantially transparent shield component may be comprised of any substantially transparent solid material such as, without limitation, certain types of plastics, clear glass, or polycarbonate material. In one embodiment, the shield component may be comprised of materials that are not toxic to human beings. The plastics that may be suitable for use in preparing the shield component may comprise, without limitation, polymethyl methacrylate, cellulose acetate butyrate, polycarbonate, or glycol modified polyethylene terephthalate (or PETG plastic). Without limitation, the shield component may be comprised of a light-weight material to facilitate contracting and expanding of the protective apparatus toward or away from the front surface of a dental chair or other object and a patient or other individual sitting in or otherwise occupying said object.

When in use, such as, without limitation, in a dentist's office, protective apparatuses of the present disclosure are intended to be positioned close to but not in contact with an individual sitting in the chair or otherwise occupying the object. In a preferred embodiment, said distance between the downward-facing surface of the shield component and the individual occupying the dentist's chair or other object may be between approximately one inch and approximately ten inches, without limitation. Other distances between the downward-facing surface of the shield component and the individual that allow for the individual remaining sufficiently comfortable and, where applicable, allow for the dentist or other healthcare worker to comfortably treat the patient, are intended to be included within the scope of this disclosure, as would be appreciated by those having skill in the art.

The substantially transparent shield component of the present disclosure 101 may exist in virtually any number of dimensions. The shield component may be approximately twelve inches to approximately six feet in length, and is preferably between approximately twelve inches and approximately two feet, six inches in length, without limitation. The shield component may be approximately twelve inches to approximately three feet in width, and is preferably between approximately twelve inches and approximately two feet in width, without limitation.

The substantially transparent shield component of the present disclosure 101 may further comprise lighting to enhance visibility for, for example, a dentist or dental assistant performing dental work inside the mouth of a patient occupying a dental chair over which the protective apparatus has been placed, as contemplated by this disclosure. Said lighting may be located, without limitation, on the downward-facing surface of the protective apparatus.

The protective apparatuses of the present disclosure may further comprise magnifying materials, such as, without limitation, magnifying glass, light emitting diodes, and/or a camera communicatively connected to, without limitation, a liquid crystal display, wherein said magnifying materials may be located within a portion of the protective apparatus at a location intended to optimally enhance visibility around the head region of an individual over whom the protective apparatus has been placed. In one embodiment of the present disclosure, said location may be approximately two-thirds of the distance from the distal end of the shield component to the proximal end of the shield component closest a connecting aspect of the handle component.

Protective apparatuses enabled by this disclosure may further comprise a camera communicatively connected to a display screen. Said display screen may, without limitation, comprise a liquid crystal display screen. Those of skill in the art will readily recognize that said display screen may comprise any number of other materials as well such as, without limitation, electroluminescent material.

The camera and display screen will now be discussed in greater detail. A camera as contemplated by the present disclosure may be positioned at virtually any number of locations within or on the protective apparatuses enabled by this disclosure. Such camera may be integrated directly into the protective apparatus 601, 701, 801, 901 or may be appended 103, 301, 501 to the protective apparatus, without limitation. Where the camera is integrated into, including where it is embedded within 601, the protective apparatus, a display screen associated with said camera may, without limitation, also be integrated 602, 702, 802, 902, 1001 into the protective apparatus, or may be appended 104 to the protective apparatus. Where the display screen and/or the camera are appended to the protective apparatus, such appendage may be effectuated using any number of joints and/or hinges, as would be readily appreciated by one of skill in the art. Where the camera is integrated into the protective apparatus, the camera lens may be located on the downward-facing surface of the protective apparatus at a location that does not obstruct the substantial transparency of the shield component and, therefore, does not impact the visibility of the patient and the visibility of the dentist's or other healthcare worker's work space.

In an alternative embodiment, the display screen may be physically separate from the protective apparatus, but still communicatively connected to camera.

Protective apparatuses of the present disclosure may further comprise a control console for controlling functioning of the camera. Such control console may comprise a series of control components 1002. Such control components may include, without limitation, a component controlling power supply to the camera (i.e., on/off), a component allowing for video and audio recording, and a component allowing for taking of still photos as well as moving images with sound.

Alternatively, a camera 103 and display screen 104 may both be included in a rotating aspect 105 operatively attached to the handle component 102 along the perimeter of the protective apparatus by any number of joints and/or hinges 106 such as, without limitation, a hinge joint or a saddle joint, or by other suitable connecting means. Said aspect connected to the protective apparatus may be rotatable along a horizontal axis. In such embodiment, the operability of the camera may correspond to the positioning of the camera. For example, positioning the camera such that the lens is facing downward through the substantially transparent shield component may cause power to be supplied to the camera thus rendering the camera operable; while positioning the camera such that the lens is facing forward or otherwise not facing downward may cause power to not be supplied to the camera rendering the camera inoperable. In this embodiment, the display screen 104 may be located on the side of the rotating aspect opposite the camera 103 so that, when in operation, a dentist working on a patient whose head region is underneath the protective apparatus may experience enhanced visibility (due to the camera) inside the patient's mouth, as displayed on the display screen 104.

As those of skill in the art will readily recognize, cameras as contemplated by the present disclosure may include high definition cameras such as, without limitation, 720p or 1080p high definition cameras. Such cameras may include an autofocus feature. Such cameras may have a digital zoom feature operable when the camera is recording video. Such cameras may be able to record and play back video in slow motion. Such cameras may comprise an image stabilization feature. The foregoing optional features are not intended to be limiting.

Display screens contemplated by this disclosure may include optional features such as backlighting and anti-reflective coating. The display screens may be virtually any number of dimensions. The display screens may be of dimensions that are conducive to integration into, or attachment to, a protective apparatus as contemplated in this disclosure. By way of illustration, the display screen may have a diagonal length of approximately six inches. Alternatively, the display screen may have a diagonal length of approximately eight inches, without limitation.

In one embodiment of the present disclosure, the protective apparatuses of the present disclosure may, without limitation, be substantially rectangular in shape, 100, 200, 300, 400, 500, 600, 700, 800, 900, 1000. As used herein, "substantially rectangular" is intended to mean two sets of two parallel sides. The junctions between the sides may form 90-degree angles or may be rounded in the immediate vicinity of the junction, or otherwise not forming a right angle. In such embodiment, one or more sides of the protective apparatus may comprise a series of LEDs 201, 302, 401, 703, 803, 903, 1003. Such series of LEDs may form a substantially linear row of LEDs. In such embodiment, each row may include 15-35 LEDs, without limitation. Each row of LEDs may, preferably, include 20-25 LEDs. LEDs of the nature described herein may comprise cool white LEDs, warm white LEDs, combo cool and warm white LEDs, amber LEDs, and/or blue LEDs, without limitation. As used herein, cool white LEDs may be LEDs where the emitted light exhibits a color temperature of approximately 4,000 Kelvin without limitation. As used herein, warm white LEDs may be LEDs where the emitted light exhibits a color temperature of approximately 3,000 Kelvin without limitation. As used herein, amber LEDs may be LEDs where the emitted light exhibits a color temperature of approximately 2,300 Kelvin without limitation. As used herein, blue LEDs may be LEDs where the emitted light exhibits a color temperature of approximately 5,750 Kelvin without limitation. Those of skill in the art will readily appreciate the functional significance of each of the foregoing color temperatures to the practice of dentistry.

In addition to these series of LEDs, protective apparatuses of the present disclosure may include up to four corner LEDs, 704, 804, 904, 1004, positioned at or near each corner, or other juncture where two sides adjoin, of a substantially rectangular protective apparatus enabled by this disclosure.

Protective apparatuses of the present disclosure may further comprise one or more control consoles for operating the LEDs, 603, 805, 1005, each comprising one or more control components 1006, 1007, 1008, 1009. In one embodiment, a protective apparatus may comprise two control consoles each comprising four control components. In such embodiment, one such control console may control output from a row of LEDs lining one or more sides of the protective apparatus, as contemplated by this disclosure. In this embodiment, one control component 1006 may control power to the row(s) of LEDs; i.e., whether these LEDs are on or off. A second of the four control components 1007 may control the color of the light emitting from the rows of LEDs. Without limitation, such colors may include cool white, warm white, a combination of cool and warm white, amber, or blue. Said colors may change upon successive manipulation of the control component; i.e., successively pressing the button or similar control component. For example, pressing this second control component once may cause the LED rows to emit cool white light; pressing this control component a second time may cause the LED rows to emit warm white light; pressing this control component a third time may cause the LED rows to emit a combination of cool and warm white light; pressing this control component a fourth time may cause the LED rows to emit amber light; and pressing this control component a fifth time may cause the LED rows to emit blue light. In this embodiment, the third 1008 and fourth 1009 control components may control the degree of intensity of light emitting from the LED rows. Without limitation, pressing the third control component may cause the light emitting from the LED rows to increase in intensity (i.e., becoming brighter) while pressing the fourth control component may cause the light emitting from the LED rows to decrease in intensity (i.e., becoming dimmer). The degree of increase or decrease in intensity of the light may be in proportion to the number of times that the third or fourth control components are pressed, up to a pre-selected maximum and down to a pre-selected minimum, respectively.

By way of further illustration, protective apparatuses of the present disclosure may comprise a second control console 606, 808, 1015 comprising one or more control components 1016, 1017, 1018, 1019. In this embodiment, a first control component 1016 may control power to one or more LEDs located at or near corners or other junctures where sides of the protective apparatus adjoin 1014; i.e., whether these such LEDs are on or off. A second of the four control components 1017 may control the color of the light emitting from these LEDs. Without limitation, such colors may include cool white, warm white, or a combination of cool and warm white. Said colors may change upon successive manipulation of this second control component; i.e., successively pressing the button or similar control component. For example, pressing this second control component once may cause these LEDs to emit cool white light; pressing this control component a second time may cause these LEDs to emit warm white light; and pressing this control component a third time may cause these LEDs to emit a combination of cool and warm white light. In this embodiment, the third and fourth control components 1018, 1019 may control the degree of intensity of light emitting from these LEDs. Without limitation, pressing the third control component may cause the light emitting from these LEDs to increase in intensity (i.e., becoming brighter) while pressing the fourth control component may cause the light emitting from these LEDs to decrease in intensity (i.e., becoming dimmer). The degree of increase or decrease in intensity of the light may be in proportion to the number of times that the control component is pressed, up to a pre-selected maximum and down to a pre-selected minimum, respectively.

The control components contemplated herein may, without limitation, be embedded into the display screen described herein and may be operable through capacitive touch, without limitation. The capacitive touch feature may be responsive even where the operator is wearing gloves as may be worn by a dentist while working on a patient, without limitation. In such an embodiment, no physical control component in the way of, for example, a conventional button is required. Alternatively, the control components contemplated herein may be operable through resistive touch or may comprise conventional buttons actuated physically.

A connecting aspect 202, 303, 604, 705 of the handle component of the protective apparatuses enabled by this disclosure may comprise a universal mount. Said connecting aspect may comprise a wide range of inside diameters. In one preferred embodiment, a connecting aspect of the handle component may be structured to accommodate a vacuum hose or other substantially cylindrical suctioning means having an outside diameter of approximately five inches, without limitation. The handle component may further comprise ventilation to help prevent objects such as, without limitation, towels or other fabrics in the immediate vicinity of, for example, a vacuum hose as contemplated herein from being sucked into said vacuum hose.

Protective apparatuses of the present disclosure may be mounted to an articulating arm. The end of the articulating arm not connected to the protective apparatus may be secured to any number of objects including, without limitation, a wall, a ceiling, or a free-standing dolly.

While various aspects of the systems of this disclosure have been described above, the description of this disclosure is intended to illustrate and not limit the scope of the system. The invention is defined by the scope of the claims and not the illustrations and examples provided in the above disclosure. Skilled artisans will appreciate additional aspects of the systems enabled by this disclosure, which may be realized in alternative embodiments, after having the benefit of the above disclosure. Other aspects, advantages, embodiments, and modifications are within the scope of the claims.

What is claimed is:

1. A rectangular protective apparatus comprising:
    a transparent shield component;
    a handle component located about a rectangular perimeter of the transparent shield component and further comprising a connecting aspect;
    a camera communicatively connected to a display screen, wherein the camera and the display screen are physically attached to the protective apparatus;
    at least three linear rows of light emitting diodes, wherein three or more sides of the protective apparatus comprise at least one linear row of light emitting diodes of the at least three linear rows of light emitting diodes, wherein said protective apparatus is operatively attached to an articulating mechanical arm, wherein said protective apparatus further comprises four junctures where four sides of the protective apparatus adjoin, and wherein the four junctures comprise one or more juncture light emitting diodes at each of the four junctures;
    a control console comprising:
        a first control component to control power to the at least three linear rows of light emitting diodes;
        a second control component to control color of light emitting from the light emitting diodes comprising the at least three linear rows of light emitting diodes;
        a third control component which, upon manipulation thereof, increases intensity of the light emitted from the at least three linear rows of light emitting diodes; and
        a fourth control component which, upon manipulation thereof, decreases the intensity of the light emitted from the at least three linear rows of light emitting diodes; and
    a second control console comprising four control components wherein:
        a first control component of said second control console controls power to the one or more juncture light emitting diodes located at each of the four junctures;
        a second control component of said second control console controls color of the one or more juncture light emitting diodes located at each of the four junctures;
        a third control component of said second control console, upon manipulation thereof, increases the intensity of the light emitted from the one or more juncture light emitting diodes located at each of the four junctures; and
        a fourth control component of said second control console, upon manipulation thereof, decreases the intensity of the light emitted from the one or more juncture light emitting diodes located at each of the four junctures.

2. The apparatus of claim 1, wherein the light emitted from the at least three linear rows of light emitting diodes comprises cool white light, warm white light, a combination of cool and warm white light, amber light, or blue light.

3. The apparatus of claim 1, wherein the light emitted from the one or more juncture light emitting diodes located at each of the four junctures comprises cool white light, warm white light, or a combination of cool and warm white light.

4. The apparatus of claim 1 wherein the camera is operatively attached to the handle component along the perimeter and integrated into the protective apparatus.

5. The apparatus of claim 4, wherein the display screen is operatively attached to the handle component along the perimeter and is integrated into the protective apparatus.

6. The apparatus of claim 1, wherein the camera is connected to the protective apparatus by a joint or hinge.

7. The apparatus of claim 1, wherein the connecting aspect comprises a substantially cylindrical aperture comprising an inside diameter of approximately five inches.

* * * * *